United States Patent [19]

Ohura et al.

[11] Patent Number: 5,543,554

[45] Date of Patent: Aug. 6, 1996

[54] PROCESS FOR PREPARING DRY CRYSTALS OF THE METHYL ESTER OF α-L-ASPARTYL-L-PHENYLALANINE, HAVING IMPROVED SOLUBILITY

[75] Inventors: Harutoshi Ohura, Yokkaichi; Akihiko Yasaki, Kawasaki; Shinichi Kishimoto, Kawasaki; Masayoshi Naruse, Kawasaki, all of Japan

[73] Assignee: Ajinomoto Co., Inc., Tokyo, Japan

[21] Appl. No.: 396,058

[22] Filed: Feb. 28, 1995

Related U.S. Application Data

[63] Continuation of Ser. No. 91,725, Jul. 15, 1993, abandoned, which is a continuation of Ser. No. 975,970, Nov. 13, 1992, abandoned, which is a continuation of Ser. No. 690,331, Apr. 26, 1991, abandoned, which is a continuation-in-part of Ser. No. 416,837, Oct. 3, 1989, abandoned, and Ser. No. 393,028, Aug. 10, 1989, abandoned, which is a continuation of Ser. No. 243,176, Sep. 8, 1988, abandoned, which is a continuation of Ser. No. 839,819, Mar. 12, 1986, abandoned, which is a continuation of Ser. No. 482,542, Apr. 6, 1983, abandoned.

[30] Foreign Application Priority Data

Apr. 12, 1982 [JP] Japan .................. 57-60671
Oct. 3, 1988 [JP] Japan .................. 63-249682

[51] Int. Cl.$^6$ ................................ C07C 227/42
[52] U.S. Cl. .................................. 560/41
[58] Field of Search ............................ 560/41

[56] References Cited

U.S. PATENT DOCUMENTS

| | | | |
|---|---|---|---|
| 4,810,818 | 3/1989 | Wakamatsu et al. | 560/41 |
| 4,831,180 | 5/1989 | Wakamatsu et al. | 560/41 |
| 4,835,301 | 5/1989 | Wakamatsu et al. | 560/41 |
| 4,835,303 | 5/1989 | Wakamatsu et al. | 560/41 |
| 4,900,863 | 2/1990 | Schmidt et al. | 560/41 |

FOREIGN PATENT DOCUMENTS

| | | | |
|---|---|---|---|
| 0091787 | 9/1985 | European Pat. Off. | 560/41 |
| 167268 | 7/1986 | Japan | 560/41 |

OTHER PUBLICATIONS

Kirk–Othmer Encyclopedia of Chemical Technology, vol. 6 (1965) 2ND Edition pp. 499–500.

McCabe et al., Unit Operations of Chemical Engineering, (1976) pp. 853–890.

*Primary Examiner*—James H. Reamer
*Attorney, Agent, or Firm*—Oblon, Spivak, McClelland, Maier & Neustadt, P.C.

[57] ABSTRACT

A process for obtaining dry crystals of α-L-aspartyl-L-phenylalanine methyl ester having a water content of about 2 wt. % to about 6 wt. % based on the weight of the wet crystals is disclosed. This process comprises exposing wet crystals of α-L-aspartyl-L-phenylalanine methyl ester, having a water content not greater than 50 wt. % based on the weight of the wet crystals and obtained by the crystallization of α-L-aspartyl-L-phenylalanine methyl ester from an unagitated solution of α-L-aspartyl-L-phenylalanine methyl ester, to a flow of air having a temperature of 80° C. to 200° C.

16 Claims, 12 Drawing Sheets

PROCESS FOR PREPARING DRY CRYSTALS OF THE METHYL ESTER OF α-L-ASPARTYL-L-PHENYLALANINE, HAVING IMPROVED SOLUBILITY

This application is a continuation of application Ser. No. 08/091,725, filed on Jul. 15, 1993, now abandoned, which is a continuation of Ser. No. 07/975,970, filed Nov. 13, 1992, now abandoned, which is a continuation of Ser. No. 07/690,331, filed on Apr. 26, 1991, now abandoned, which is a continuation-in-part of Ser. No. 07/416,837, filed on Oct. 3, 1989, now abandoned, and Ser. No. 07/393,028, filed on Aug. 10, 1989, now abandoned, which is a continuation of Ser. No. 07/243,176, filed on Sep. 8, 1988, now abandoned, which is a continuation of Ser. No. 06/839,819, filed on Mar. 12, 1986, now abandoned which is a continuation of Ser. No. 06/482,542, filed on Apr. 6, 1983, now abandoned.

BACKGROUND OF THE INVENTION

1. Field of the Invention

The present invention relates to processes for preparing dry crystals of α-L-aspartyl-L-phenylalanine methyl ester (aspartame).

2. Discussion of the Background

Aspartame is a refreshing sweetener which has the salient advantage of having a very low level of the bitter taste or aftertaste generally found in highly sweet sweeteners. It has thus found wide use as a low calorie sweetener.

In terms of its physical properties however, aspartame suffers from poor dispersibility and solubility in water. To obtain aspartame having excellent solubility, investigators have tried to form it into granules, effervescence foam tablets and the like by combining it with excipients or disintegrators.

However, the presence of these excipients, etc., is often troublesome depending upon the intended use of the product. A high purity aspartame product with good solubility characteristics is thus in strong demand.

Attempts have been made towards improving the solubility of aspartame while maintaining its purity. These attempts include a method which comprises spray-drying aspartame in its slurry state (Japanese Patent Publication No. 58-20588), a method which comprises adding water to aspartame in a specific water content and granulating the aspartame (Japanese Patent Application Laid-Open No. 59-95862), etc.

With respect to the solubility of aspartame crystals per se, the $I_B$ type crystals disclosed in Japanese Patent Application Laid-Open No. 59-172444 have good solubility as dry crystals. ($I_B$ type aspartame crystals are described in detail in EP 0 119 837 and U.S. Pat. No. 4,579,747.) However there is still a need for a method to obtain pure $I_B$ type crystals on an industrial scale. To date no such process for obtaining high purity $I_B$ type crystals is available.

SUMMARY OF THE INVENTION

Accordingly it is an object of this invention to provide a process which does not suffer from the above-noted drawbacks.

The present invention provides a process for obtaining dry crystals of α-L-aspartyl-L-phenylalanine methyl ester which satisfies this object and other objects which will be apparent from the description of the invention given below.

(i) exposing wet crystals of α-L-aspartyl-L-phenylalanine methyl ester, having a water content not greater than 50 wt. % based on the weight of the wet crystals and obtained by the crystallization of α-L-aspartyl-L-phenylalanine methyl ester from an unagitated solution of α-L-aspartyl-L-phenylalanine methyl ester, to a flow of air having a temperature of 80° C. to 200° C.; and (ii) obtaining α-L-aspartyl-L-phenylalanine crystals having a water content of about 2 wt. % to about 6 wt. % based on the weight of the dry product.

BRIEF DESCRIPTION OF THE FIGURES

A more complete appreciation of the invention and many of its attendant advantages will be readily obtained as the same becomes better understood by reference to the following detailed description when considered in connection with the accompanying figures, wherein.

DETAILED DESCRIPTION OF THE PREFERRED EMBODIMENTS

The inventors have found that high purity $I_B$ type aspartame crystals in which excipients, foaming agents, ec., are absent, can be obtained by drying wet crystals of aspartame at a relatively low temperature of below 80° C. However drying wet crystals of aspartame at a low temperature of below 80° C. requires a long period of time. This characteristic makes such a method inefficient from an industrial viewpoint.

Further to obtain high purity $I_B$ type crystals, complicated operational controls are also required. From both technical and economical viewpoints, there is thus a distinct need for a process for continuously preparing $I_B$ type aspartame crystals having excellent solubility efficiently, e.g., in a short period of time.

As a result of extensive investigations aimed at solving the above problems, the present inventors have now found that by controlling (a) the water content of aspartame wet crystals to be dried (i.e. using crystals obtained by a crystallization process in which aspartame is crystallized from an unstirred solution) to a specific maximum amount, and (b) drying these wet crystals under specific conditions, $I_B$ type aspartame crystals having good solubility characteristics are readily obtained on an industrial scale.

In this present process the wet crystals are dried with hot air, by exposing the wet crystals to hot air having a temperature of 80° C. to 200° C., the temperature of the hot air being measured prior to its contact with the wet aspartame crystals.

The wet aspartame crystals used are obtained as the crystallization product of an unagitated (unstirred) solution. For example one may use the method for crystallization disclosed in Japanese Patent Application Laid-Open No. 58-177952 or the method of U.S. patent application Ser. No. 06/839,816, the latter method being outlined hereinbelow.

More specifically, this method comprises a step of cooling an aqueous solution of dissolved aspartame without stirring (i.e. without affecting forced flow in the solution) to obtain a pseudo solid phase of aspartame. Cooling is achieved by conductive heat transfer without affecting forced flow such as mechanical stirring, etc.

The process is carried out in such a way that, after the cooling operation, the crystallized pseudo solid phase obtained is obtained in an amount of approximately 10 grams or more of pseudo solid per liter of crystallization solvent. After the pseudo solid phase is formed, the solid is subjected to solid-liquid separation as it is. Or, if desired or necessary, after further cooling, the solid-liquid separation is performed. Thus, the aspartame wet crystals used in the present process are obtained from an unagitated (non-stirring) crystallization process. This crystallization process is discussed in greater detail and specific examples are provided infra.

Aspartame crystals obtained by the unagitated crystallization process are composed of bundles of fine needles. These fine needles are bundle-like crystals which give the material the appearance of forming one crystal mass. They show very good dehydration properties in solid-liquid separation operations.

On the other hand, according to the inventors' work, if crystallization is carried out with stirring, the procedure most widely used industrially, the water content of the filtered wet crystals obtained is approximately 75%. Processes carried out with stirring comprise affecting forced flow in the crystallization solution, such as by mechanical stirring, etc., during crystallization of the aspartame from the aqueous aspartame solution with cooling. With such processes one obtains mixtures of slurry-like mother liquors and needle-like crystals.

Even with centrifugation, the water content of wet aspartame crystals obtained from processes which use stirring is still a little over 50% by weight. Therefore, when such wet aspartame crystals (obtained by crystallization with stirring) are charged into a jet air drier apparatus, etc., as they are, adherence of the wet crystals to the inner wall of the drier apparatus is unavoidable. Consequently over-drying of the adhered crystals and scorching occurs. This results in fatal disturbances in the operation of making commercial products, making the process commercially flawed.

Further since the dispersibility of these wet crystals in an air flow is poor, the chance of forming disadvantageous large agglomerated masses increases. Upon feeding the wet crystals into a drier apparatus, the wet crystals also adhere to the feeding screw so that quantitative feeding is impeded.

In sharp contrast, the wet aspartame crystals obtained from the unagitated (non-stirring) crystallization process can be readily fed to an air flow drier apparatus, after centrifugation, as they are. The water content of these crystals is generally 20 to 50 wt. %, and when they are subjected to further centrifugation, their water content is approximately 10 to 20 wt. %.

Even when such crystals having a water content of 20 to 50 wt. % are directly fed into the air flow apparatus, the problems set out above found with crystals obtained from the process of crystallization with stirring are absent, and the drying operation can be carried out smoothly to efficiently obtain high purity $I_B$ type aspartame crystals. The wet aspartame crystals which can be used in the present process also include granules of aspartame in a wet crystalline state (that is, granules obtained by extruding the wet crystals through a screen).

Devices for continuously drying the wet crystals while exposing them to hot air which can be used in the present process include driers conventionally used for continuous air drying such as pneumatic conveyor dryers, air jet driers, micron driers, etc. Any kind of such driers may be used.

When a pneumatic conveyor dryer is used, dryer speed the thickness of the wet crystalline composition being dried are not important or critical. Rather it is the air temperature which is important.

When aspartame is dried at a high rate of drying, a part of the aspartame product tends to be converted into diketopiperazine derivatives. The formation of these derivatives which are not sweet at all, results in loss of sweetness in the product.

In the present process, hot air drying is carried out continuously, and, for a given unit volume of sample of wet crystals drying is completed over a period of time as short as about one minute. That is, the residence time of a given unit volume of the crystals during the drying operation is as short as about one minute. Under these conditions, even though the hot air used is of an inlet temperature of as high as 80° C. to 200° C. more desirably 130° to 160° C. and an outlet temperature of 50° C. to 180° C., more preferably 70° C. to 130° C., there is little formation of diketopiperazine derivatives, and the formation of type II crystals (described in Japanese Patent Application Laid-Open No. 59-172444) is minimized.

Accordingly, with the present process $I_B$ type aspartame crystals can be prepared stably with extremely good efficiency. If the temperature of the hot air used is below 80° C., a long period of time is required for the drying operation. Conversely when the temperature used is higher than 200° C., the rate of rearrangement to type II crystals increases. Therefore, temperatures outside the range used in the invention are not preferred for the stable industrial preparation of $I_B$ type crystals.

Dry $I_B$ type aspartame crystals having a water content of approximately 2 to 6 wt. % can be obtained by the continuous drying while sending hot air. The $I_B$ type aspartame crystals obtained have good solubility characteristics and display excellent powder properties having minimal scattering properties during handling.

Other features of this invention will become apparent in the course of the following descriptions of exemplary embodiments which are given for illustration of the invention and are not intended to be limiting thereof.

EXAMPLES

Example 1

A raw aqueous solution (380 liters) containing 17.7 kg of dissolved aspartame (having, at 55° C., an initial aspartame concentration of 4.4 wt. %) was charged into a crystallization device having a diameter of 400 mm equipped with a cooling jacket and an internal cooling plate. A coolant having a temperature of 0° C. was cycled through the cooling jacket and the internal cooling plate to cool the solution without agitation over 3 hours. After about an hour of cooling, the solution, as a whole, became a pseudo solid phase.

The aspartame crystals in the pseudo solid phase were transferred to a receiving tank equipped with a stirrer and homogenized to a slurry. The slurry was further cooled (from an initial temperature of 16° C. to a final temperature of 7° C. in the receiving tank).

The thus obtained slurry was filtered and dehydrated with a centrifuge having a diameter of 36 inches to give wet aspartame crystals having a water content of 30 wt. %. The wet crystals obtained by this unagitated crystallization (i.e. in which there was no stirring of the solution) were then dried by continuously feeding them to a micron drier (manufactured by Hosokawa Micron Co., Ltd.) using a screw feeder.

| Drying conditions used: | |
|---|---|
| Temperature of hot air at drier inlet | 135° C. |
| Temperature of waste air at drier outlet | 104° C. |

The yield of the $I_B$ type aspartame crystals obtained after drying was determined by calculating the ratio of characteristic X-ray powder diffraction pattern peaks for the $I_B$ type crystals and the II type crystals. (The yield of $I_B$ type aspartame crystals was similarly calculated in the examples.)

| Results: | |
|---|---|
| Water content | 2.6 wt. % |
| Yield of $I_B$ type aspartame crystals | 95% |
| Diketopiperazine derivatives | less than 0.05 wt. % |

Example 2

Wet aspartame crystals (having a water content of 30 wt. % based on the weight of wet aspartame crystals) were obtained by using an unagitated crystallization process similar to that set out in Example 1. The wet crystals were fed to the same micron drier used in Example 1 and air dried under the drying conditions set out below.

| Drying conditions: | |
|---|---|
| Temperature of hot air drier inlet | 160° C. |
| Temperature of waste air at drier outlet | 109° C. |
| Results: | |
| Water content | 2.4 wt. % |
| Yield of $I_B$ type aspartame crystals | 87% |
| Diketopiperazine derivatives | less than 0.05 wt. % |

Discussion of the Unagitated (Non-Stirring Crystallization Process used in the Present Invention for obtaining Wet Crystals of Aspartame:

Table 1 below shows the powder properties of aspartame crystals obtained by the unagitated crystallizing process used in the present invention (see Example 1) and those properties for crystals obtained by a process which uses agitation (see the Comparative Example).

TABLE 1

| | Agitated Process | Unagitated Process |
|---|---|---|
| Static specific volume (cc g$^{-1}$) | 6–7 | 3–4 |
| Close specific volume (cc g$^{-1}$) | 3–4 | 2–3 |
| Rate of dissolution for the same volume of aspartame crystals | 14–17 | 5–6 |

In crystallizing aspartame from an aqueous solution having at least a certain minimum concentration of aspartame by cooling without stirring, APM crystals take up the solvent into the space formed among them, resulting in the whole solution giving the appearance of having formed a sherbet-like pseudo solid. The crystals thus obtained show extremely good properties in subsequent solid-liquid separation operations. Observation of the crystals under a scanning type electronmicroscope revealed several needle-like crystals bundled together to form an apparent single crystal.

These bundle-like crystal aggregates are extremely resistant toward physical impact as long as they are not formed in a supersaturated solution. They have been confirmed to maintain a 5- to 10-fold or more diameter as compared to that of conventional crystals, even after being transported, separated or dried. More surprisingly, even though under similar crystallizing conditions crystals of ordinary substances deposit on the heat-transfer surface(s) of the crystallization equipment to form difficult to remove scales, precipitation of the aspartame crystals using an unagitated process provides a crystalline product which is easily and completely removed from the cooling surface(s).

Aspartame crystals obtained from an aspartame solution by cooling the solution under conditions forming a pseudo solid phase possess good separability, providing salient industrial economical advantages. Once the solution takes a pseudo solid phase, it maintains its good separability characteristics even when subjected to a desupersaturation procedure of rapid cooling accompanied by forced flow, which serves to increase the efficiency of the step and improve crystallization yield. Unagitated cooling means that the cooling operation is conducted without forced flow being caused, for example, by mechanical stirring.

Figure 1A:
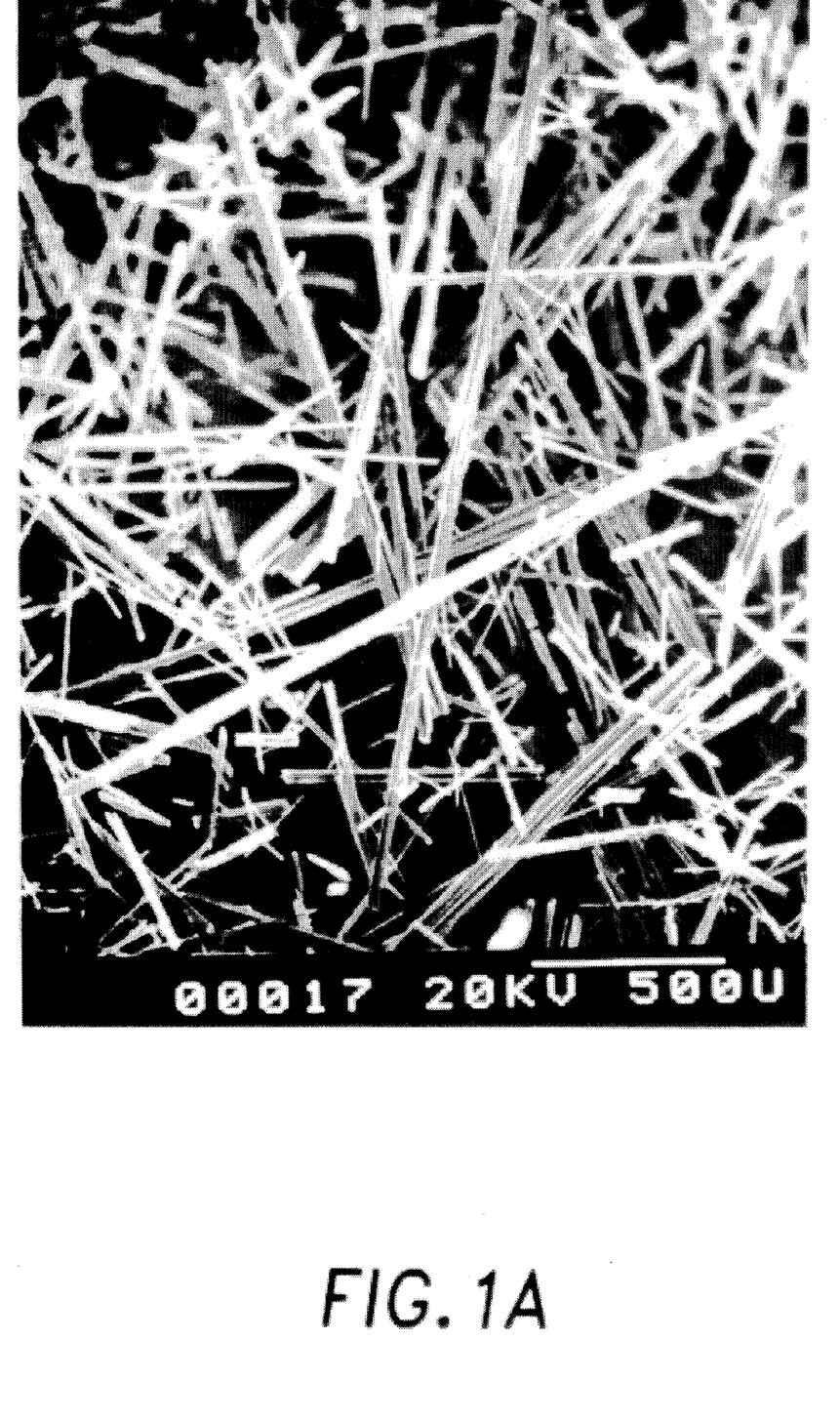
FIG. 1A nd FIG. 1B are electronmicroscopic photographs of crystals obtained by the unagitated capitalization process used in the present invention.
Figure 1B:
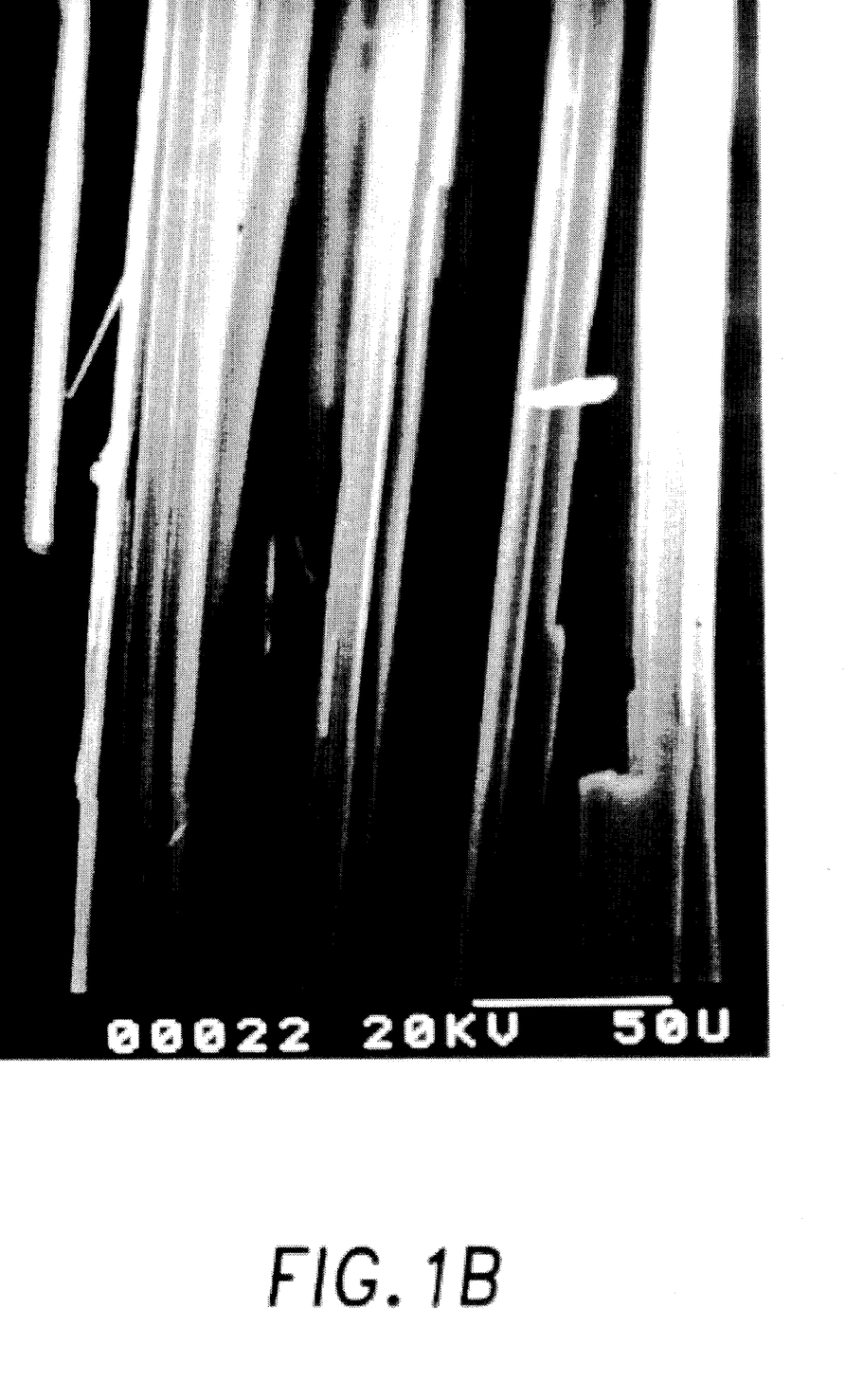
Figure 2A:
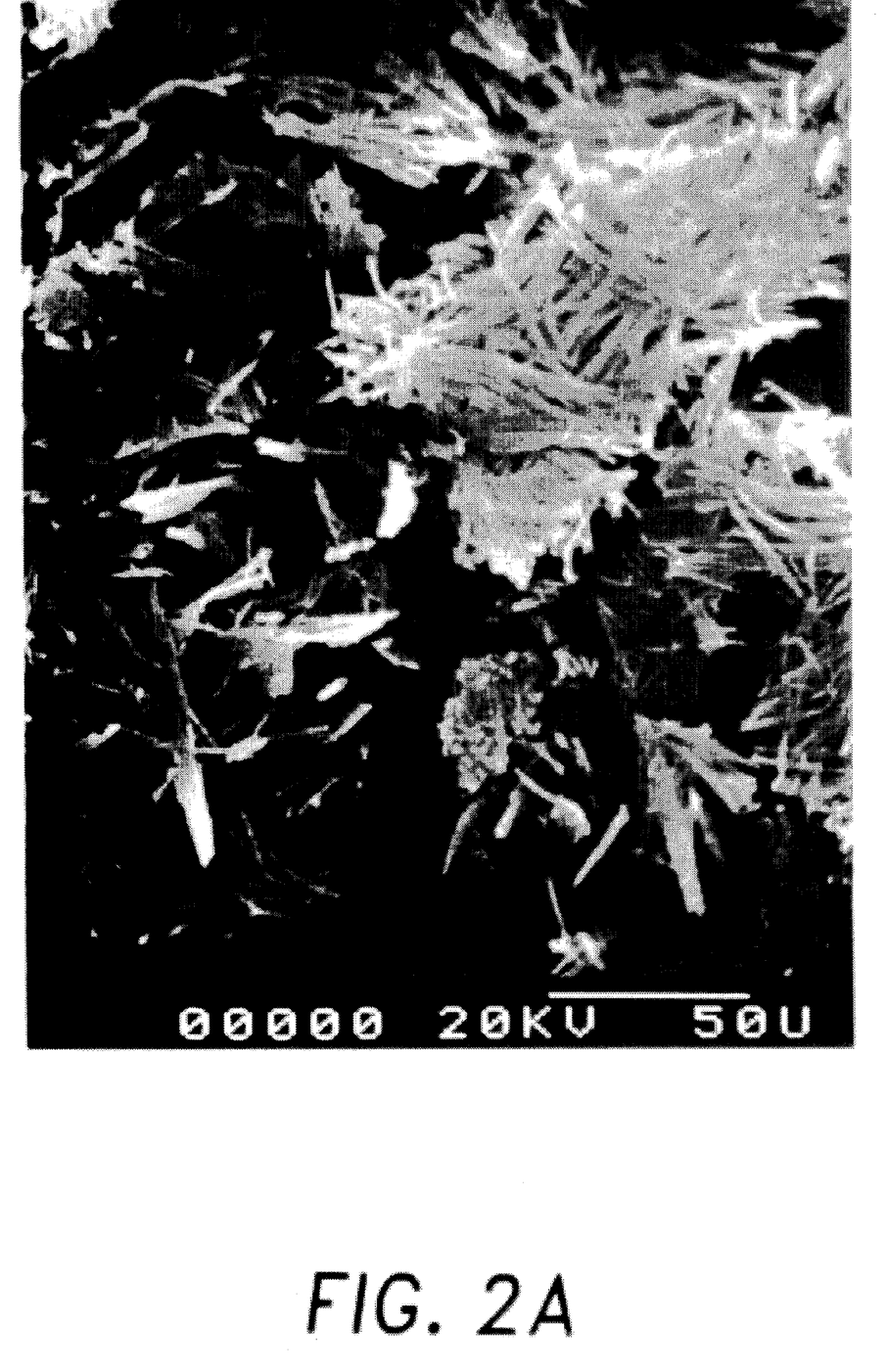
FIG. 2A and FIG. 2B are electronmicrographs of aspartame crystals obtained by an agitated crystallization process.
Figure 2B:
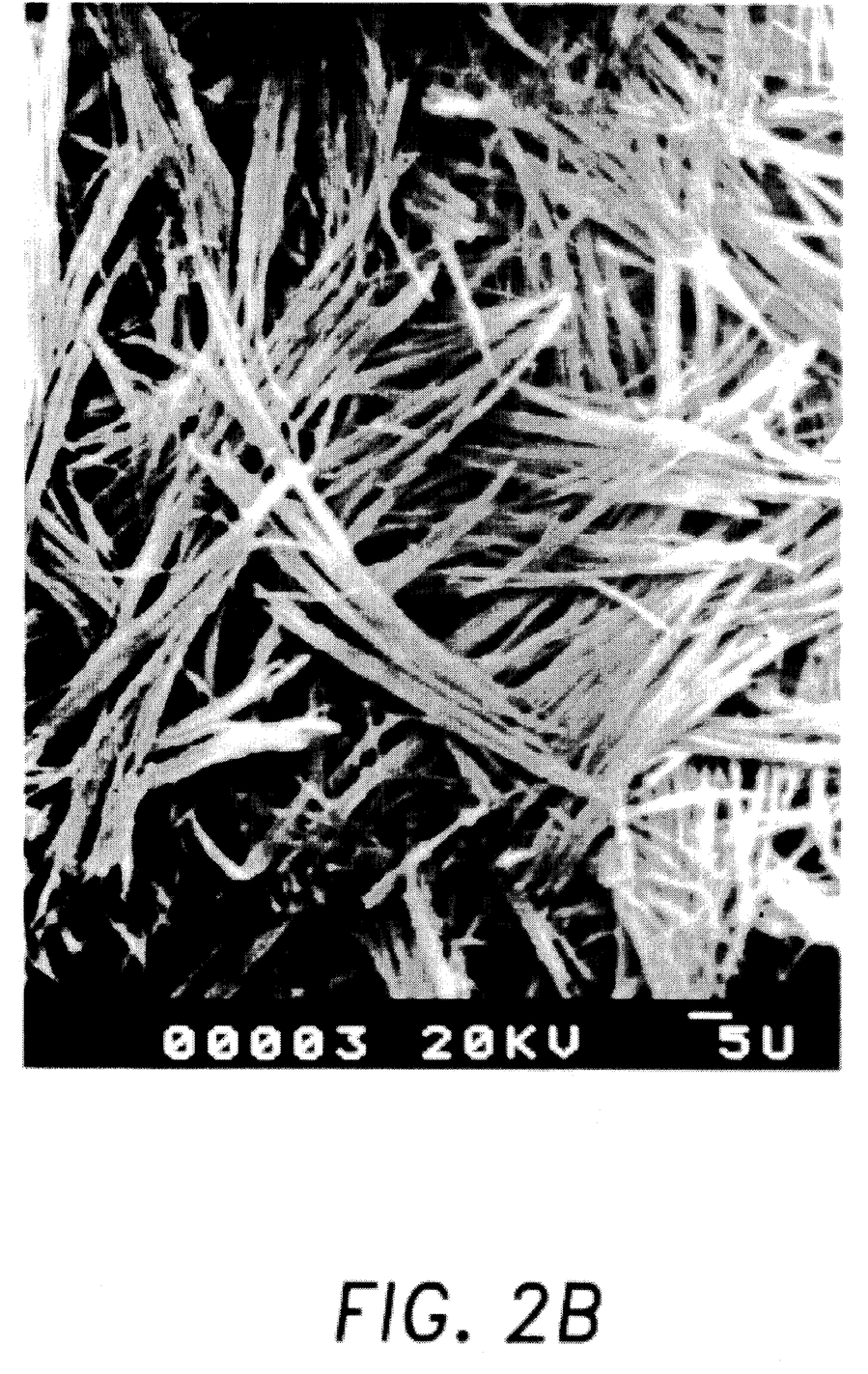
Figure 3A:
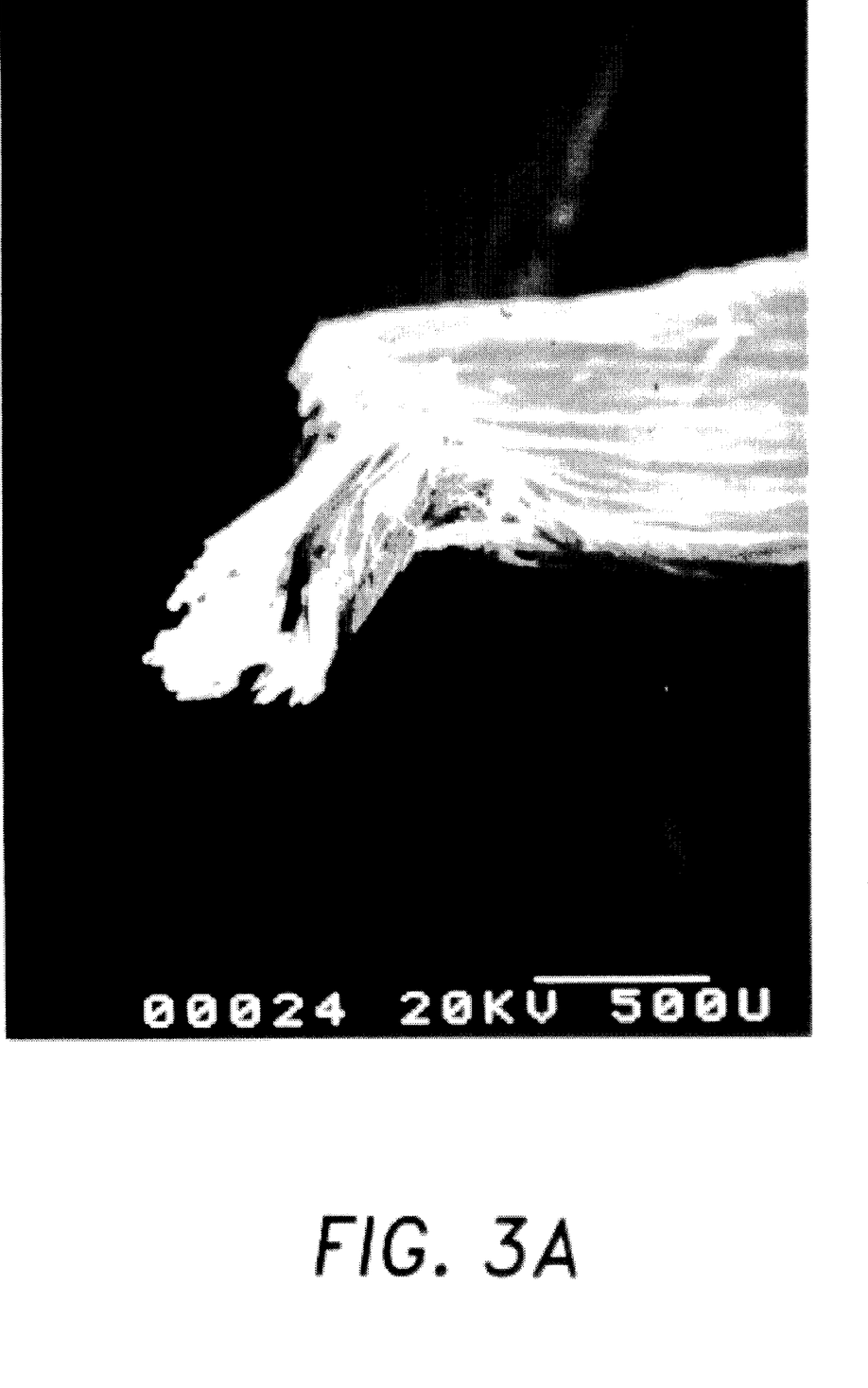
FIG. 3A and FIG. 3B are electron microscope photographs of aspartame crystals obtained from a crystallization process in which forced flow is absent but under such condition that no sherbet is formed.
Figure 3B:
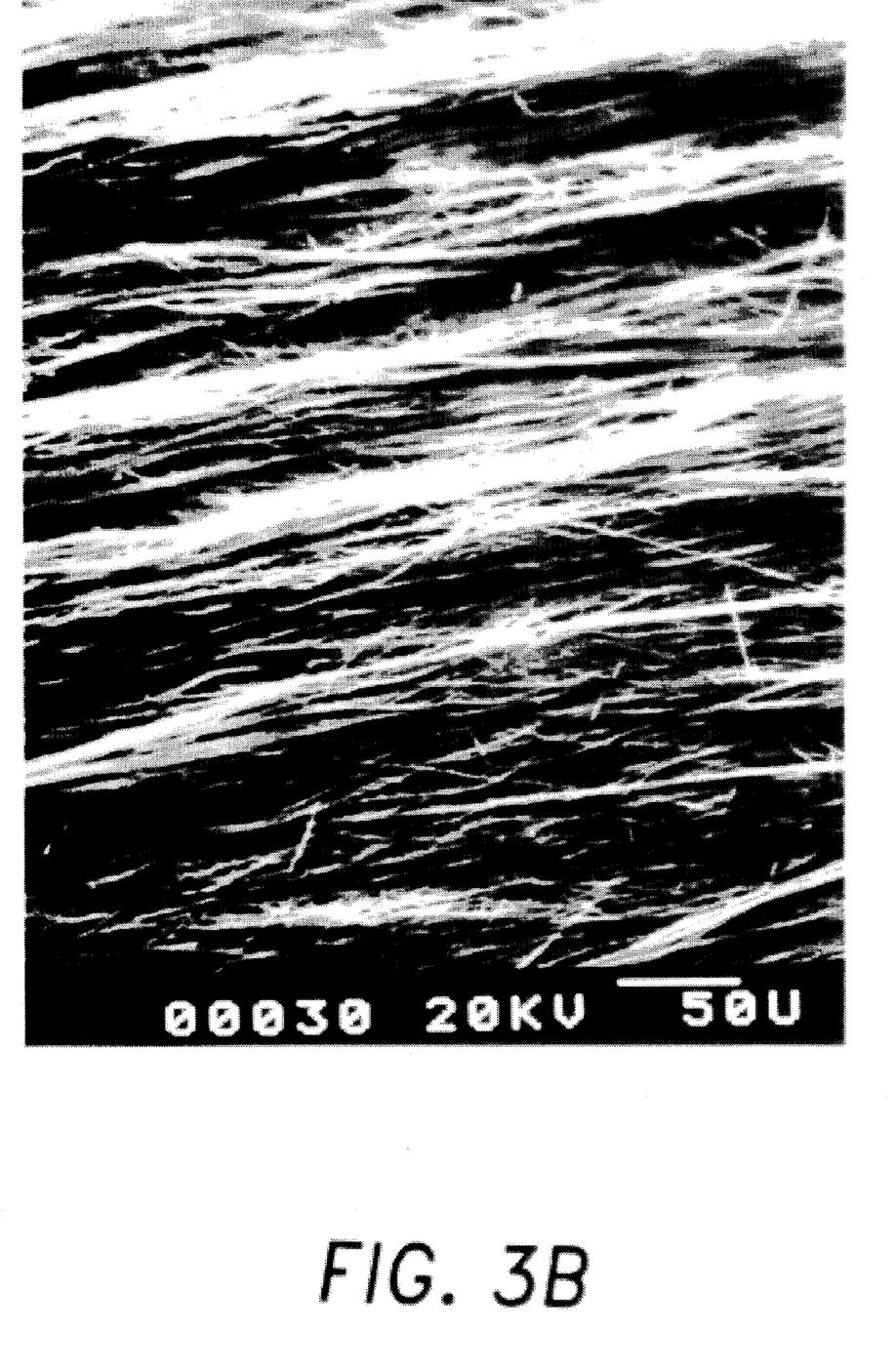

It is desirable to obtain the sherbet-like pseudo solid phase as fast as possible. For the purpose of comparison, some of the Figures provide-electronmicroscopic/photographs of bundled crystals: (i) obtained by the unagitated process (FIG. 1A (x58) and FIG. 1B (x580), (ii) fine crystals obtained by indirect cooling under forced flow (FIG. 2A x560) and FIG. 2B (x1,280)), and (iii) dendrite crystals obtained without causing forced flow and under such condition that no sherbet is formed (FIG. 3A (x51) and FIG. 3B (x350)). These photographs shows three crystal types, which show the same results in X-ray powder diffractometry, but which are clearly different from each other in shape and size due to the difference in crystallizing parameters used.

Figure 4:
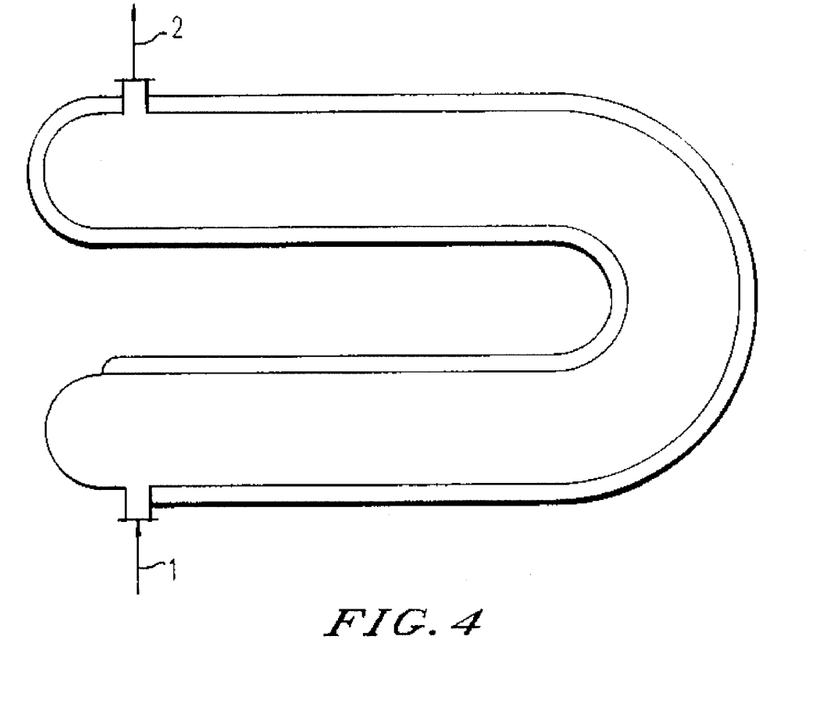
FIGS. 4, 5, 6, and 7 show examples of crystallizers which can be used in the unagitated crystallization process used in the present invention.

FIG. 4 provides an example of continuous crystallizers which can be used. This crystallizer uses a jacketed U-tube having nozzles on both ends. Upon initiation of the crystallizing procedure, a feed solution is previously charged in the tube before initiation of cooling. At a Stage where crystallization has proceeded in the tube, a feed solution is transferred to the tube through feed inlet 1 at a slow rate, upon which a sherbet-like slurry is discharged out of the tube through opposite outlet 2. The sherbet-like slurry can be continuously obtained onward by cooling through heat transfer by conduction and feeding the solution at such flow rate that a sufficient residence time for crystallization to be completed is provided.

The crystallizer which may be used need not necessarily be a U-tube. Vertical or horizontal straight tube or any curved tube that does not suffer pressure loss more than is necessary may be employed as well.

Figure 5:
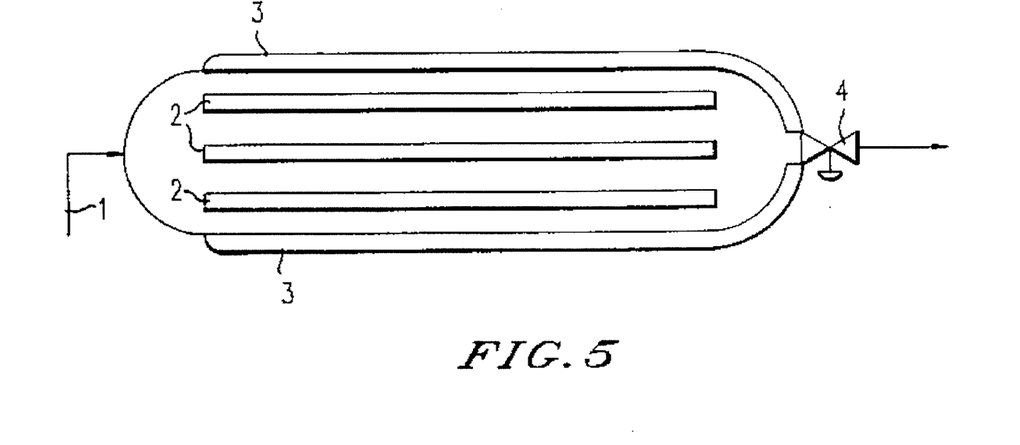

FIG. 5 shows an example of a bacthwise crystallizer which can be used. A feed solution is introduced through feed inlet 1. After completely charging the solution, a refrigeration medium is introduced into cooling plates 2 or cooling tube and jacket 3 to cool the solution. After a predetermined period of time, discharge valve 4 is opened to discharge the sherbet-like slurry.

Figure 6:
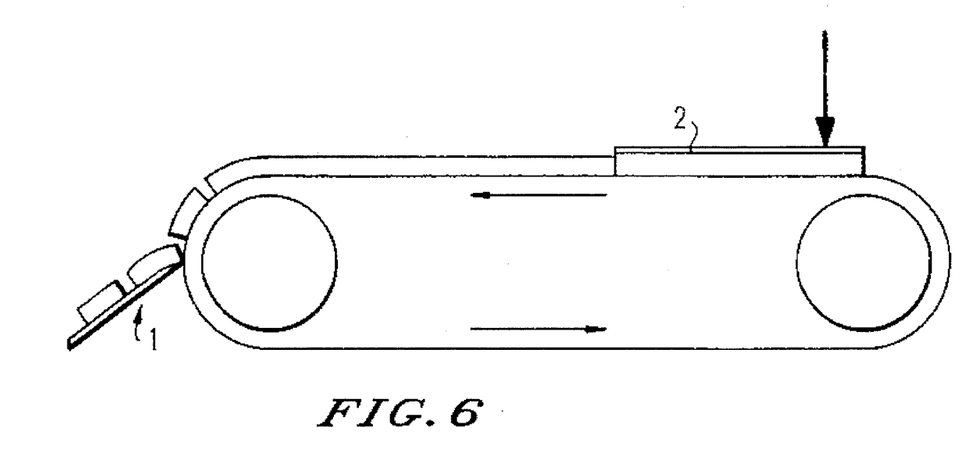
Figure 7:
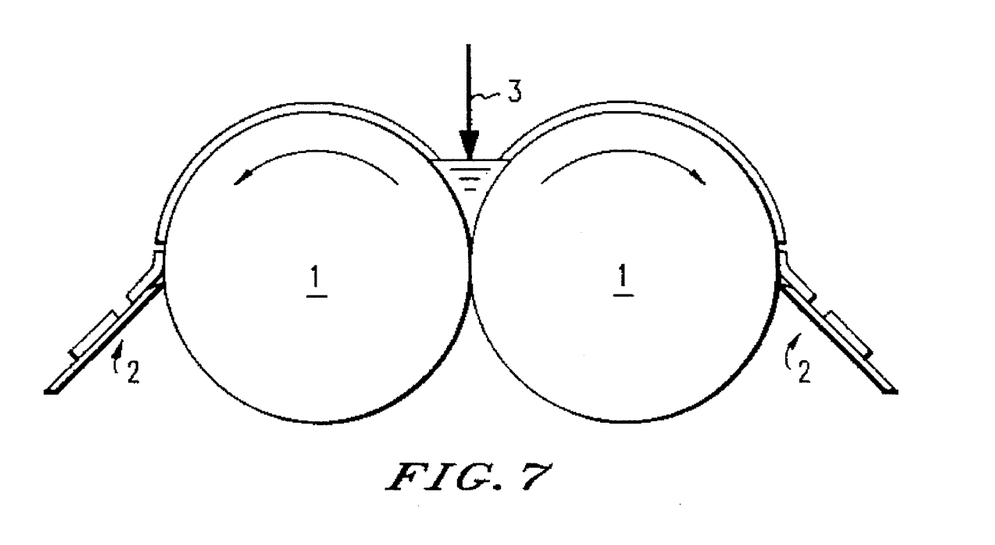

FIGS. 6 and 7 show examples of conducting the process of the present invention using a conventional apparatus. The procedures are continuous in both cases.

In FIG. 6, a rotating steel belt is used as a cooling surface (the belt being cooled, for example, by blowing a refrigeration medium to the back of the belt), and a feed solution is continuously introduced onto the belt to crystallize. The sherbet-like slurry formed is recovered by scraping with scraper 1 provided on the other end. In this embodiment, for the purpose of forming a thick sherbet layer on the belt, guides 2 may be provided on the sides of the belt, or a frame may be fixedly provided on the belt to thereby prevent the solution from flowing over before solidifying. In some cases, a semi-continuous procedure may be employed.

FIG. 7 shows utilizing an evaporate-condenser. A feed solution is introduced to the center 3 of two contact-rotating drums 1 rotating outward. The drums are cooled from inside with a refrigeration medium instead of being heated from inside with steam, on which sherbet depsits as a result of crystallization. The thus formed sherbet is scraped by scraper 2.

To obtain the sherbet-like pseudo solid, apparently solidified state, the unagitated crystallization solution must contain, at the end of crystallization, about 10 grams or more of solid per liter of solvent. That is, in an aqueous solution system, a satisfactory recovery of aspartame can be attained by cooling the system to 5° C. Taking the solubility of aspartame into consideration, theoretically, an initial concentration of aspartame solution before crystallization of 1.5 wt % suffices since the saturation concentration at this temperature is 0.5%.

However, in the low supersaturated region, crystallizing rates are too slow. Therefore, from a practical viewpoint the aqueous system must contain about 2 wt % or more of aspartame to form the sherbet.

To obtain crystals having large diameters, solidification must proceed at a faster rate. For this purpose, the initial concentration is desirably about 3 wt % or more.

On the other hand, the upper limit of the concentration which can be used depends upon the stability of aspartame in solution at elevated temperatures. In an aqueous system, a concentration of about 10 wt % or less, which is a saturation concentration of aspartame at 80° C., is usually a suitable upper limit.

Water can be used as the crystallizing solvent. But this water may optionally contain other inert solvents.

The cooling rate used in the unagitated crystallization process is an important procedure factor. However, in heat transfer through conduction, a temperature distribution appears within a solution being cooled, and the cooling rate is not constant as a function of time. Thus definite control of the cooling rate is difficult.

However, a workable average temperature of the cooled solution after a given period of time may be defined by the temperature of the refrigeration medium used, the initial temperature of the cooled solution, and the maximum distance between the cooled solution and the heat-transfer surface.

Any known refrigeration medium may be used, such as propylene glycol, ethylene glycol or cooling water. The temperature of the refrigeration medium is most suitably −5° C. to 35° C. to prevent freezing of the solvent and to obtain an appropriate cooling time. Further, the greater distance between a given unit volume of the cooled solution and the heat-transfer surface, the more one notes a difference in crystallization degree due to greater range of temperature distribution within the cooled solution. In addition, aspartame is subject to decomposition resulting in that a predetermined supersaturation cannot be attained, adversely affecting separability. Therefore, a given unit volume of the remotest part of the solution being cooled is desirably 500 mm or less from the heat-transfer surface. Those skilled in the art, through simple preliminary experiments, can easily find conditions necessary for rendering the whole solution into a pseudo solid phase in the illustrated crystallizers.

The thus obtained sherbet-like pseudo solid phase comprising aspartame crystals and the solvent does not itself show fluidity, but shows extremely good separating properties from the cooling surface, thus causing no trouble during discharge from the crystallizer. It can be easily destroyed into a slurry, for example, by stirring, and it can be transported through pumps or the like.

Additionally, in the process of the present invention, since cooling of the system is conducted through heat transfer by conduction, a longer time is required to cool the solution to a desired temperature than is needed with cooling under forced flow. The present process however provides more than enough advantages to compensate for this disadvantage. However, to raise efficiency even more and improve yields, it is possible to conduct a desupersaturating procedure subsequent to the aforesaid crystallizing step.

That is, the sherbet-like pseudo solid phase obtained by crystallization through heat transfer by conduction and comprising APM crystals and the solvent is rapidly cooled subsequent to destruction of the solid phase, for example, by stirring to remove residual supersaturation in a short time. However, where the proportion of aspartame crystals additionally precipitated in the desupersaturating procedure accounts for about 25% or more of the whole solid phase of APM finally obtained, solid-liquid separability of the slurry is sharply deteriorated. Therefore, desupersaturation is desirably controlled to less than the above-described degree.

The unagitated crystallization process of present invention will now be described in more detail by the following non-limiting examples of preferred embodiments of the present invention.

Example 3

Figure 8:
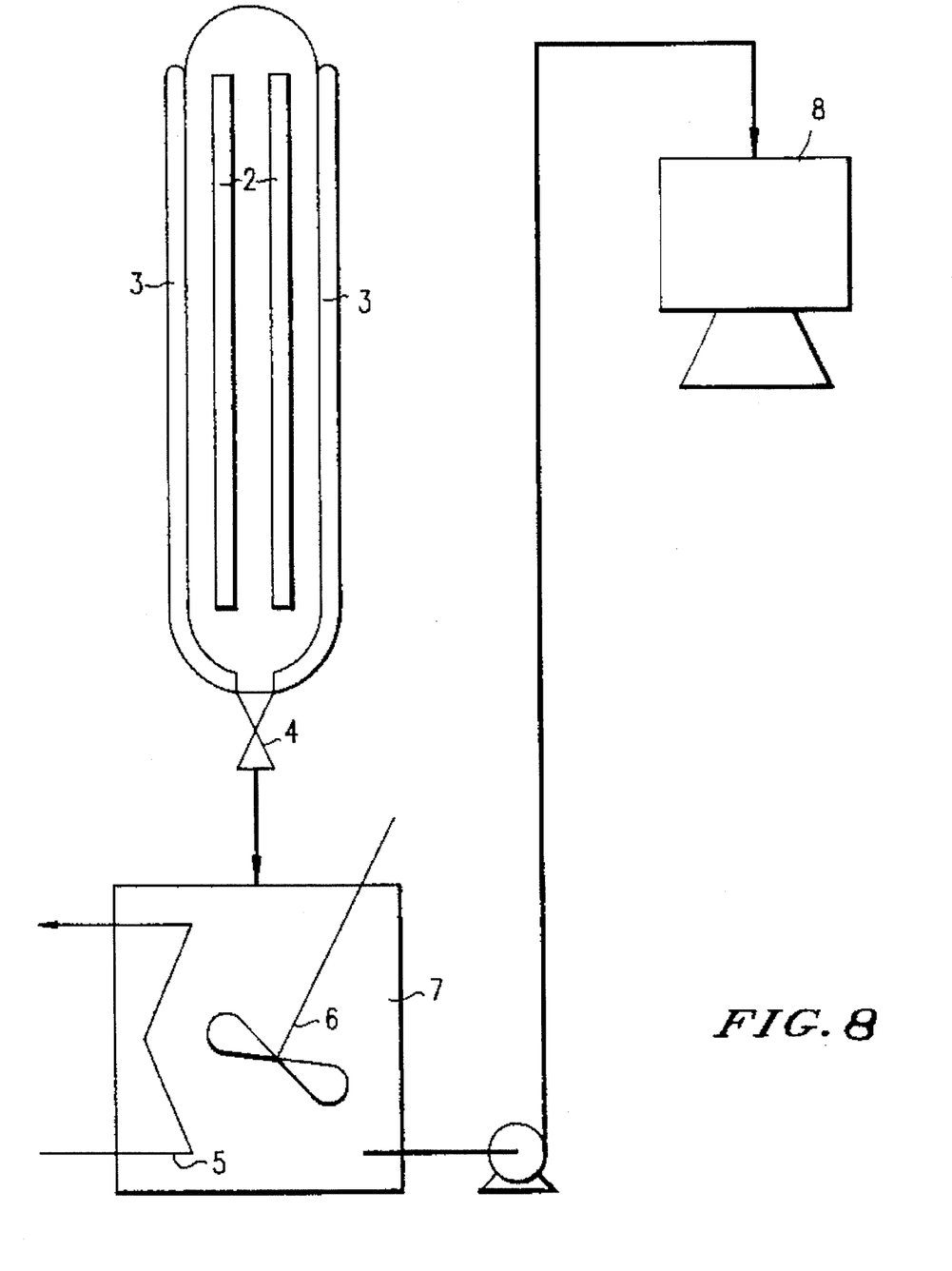
FIG. 8 shows the crystallizer used in example 1.

This example was conducted using the apparatus shown in FIG. 8.

A feed solution (380 liters) containing 17.7 Kg of dissolved aspartame (containing 3% DKP)(55° C.; initial concentration of aspartame 4.4 wt %) was charged in a stainless steel crystallizer having a diameter of 400 mm (maximum distance between the cooled solution and the cooling surface: 75 mm) equipped with a jacket 3 and inner cooling plates 2. A 0° C. refrigeration medium was circulated through the jacket and the cooling plates to conduct cooling for 3 hours. Cooling through heat transfer by conduction became predominant about 15 minutes after initiation of the cooling. The whole solution became a pseudo solid phase after about one hour.

Thereafter, the contents of the crystallizer were discharged into tank 7 equipped with cooling coil 5 and stirrer 6 where the solid phase was destroyed. The average temperature of the slurry was about 16° C., and the aspartame concentration of the mother liquor was 0.9 wt %. Then, a refrigeration medium was introduced into coil 5 under further stirring to conduct cooling for one hour to lower the temperature of the slurry to about 7° C. The aspartame concentration of the mother liquor at this point was 0.7 wt %.

The slurry obtained was filtered and dewatered using a centrifugal separator 8 having a diameter of 36 inches; the water content of the cake decreasing to 25% only after 20 minutes. Yield: 19 Kg (wet); recovery ratio: 86%; DKP content: 0.1%.

Additionally, aspartame crystals additionally precipitated in the desupersaturation procedure accounted for about 5% of the whole solid phase finally obtained.

Similar results were obtained by crystallizing aspartame using an apparatus having cooling tube in place of the cooling plate.

With a slurry obtained by a conventional process (see Comparative Example 1 below), the water content was as high as 45 to 50% even after 2 hours of filtration and 1 hour of dewatering (3 hours altogether).

Comparative Example

Figure 9:
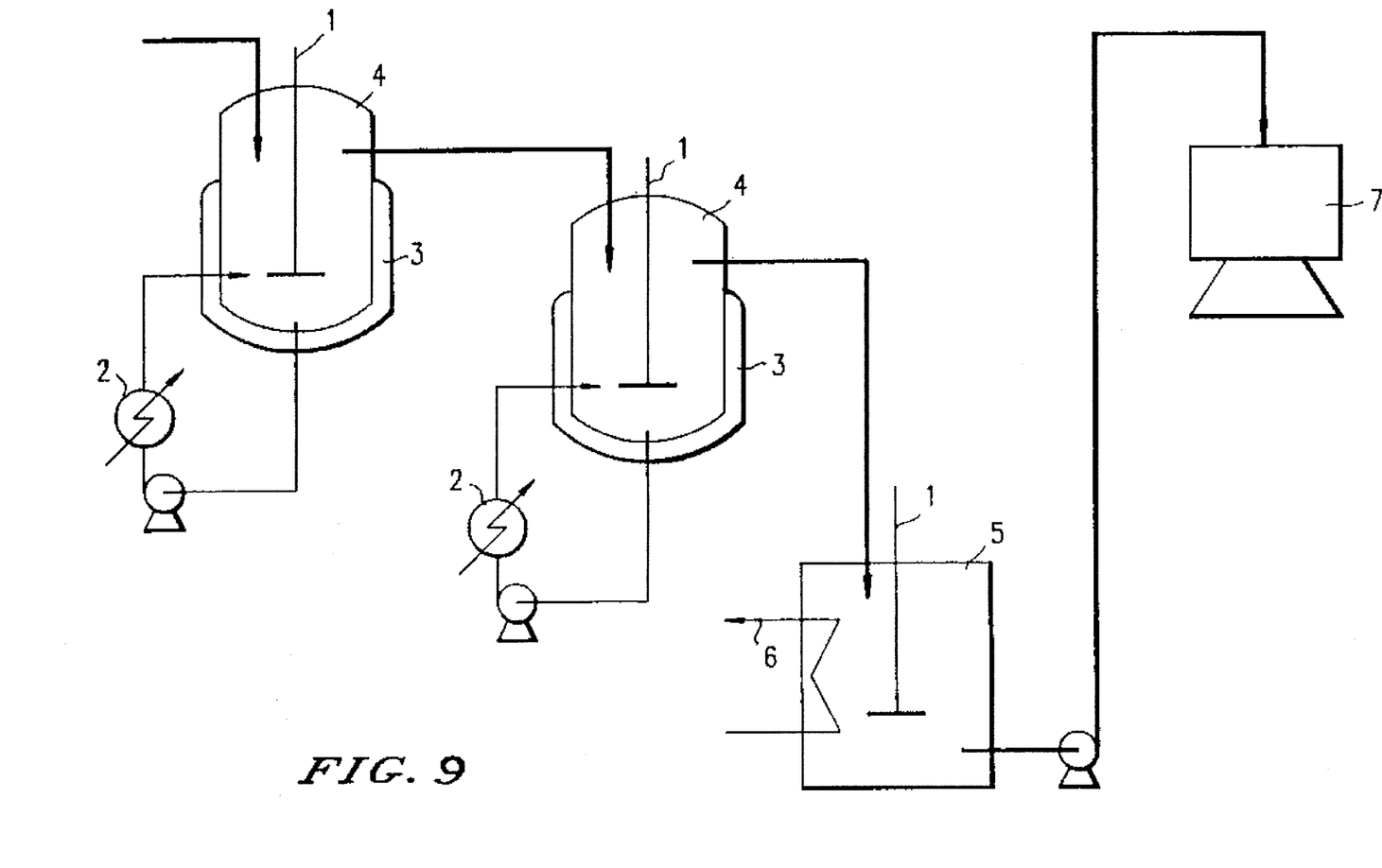
FIG. 9 shows a crystallizer used in an agitated crystallization process.

This comparative example was conducted using the apparatus shown in FIG. 9. A feed solution was continuously introduced through feed inlet 8. Two stainless steel tanks 4 (volume: 100 liters) equipped with a stirrer 1, an outer heat-exchanger 2, and jacket 3 were used in series. A stirring speed of 50 r.p.m. was used. The aspartame concentration of the feed solution was 4.4 wt %, and the flow rate was 60 liters—1 hr. The average temperature in the first tank was 25° C., that in the second tank 10° C. Additionally, in FIG. 9, numeral 5 designates a receiving tank equipped with stirrer 1 and cooling coil 6, and 7 designates a centrifugal separator.

Figure 10A:
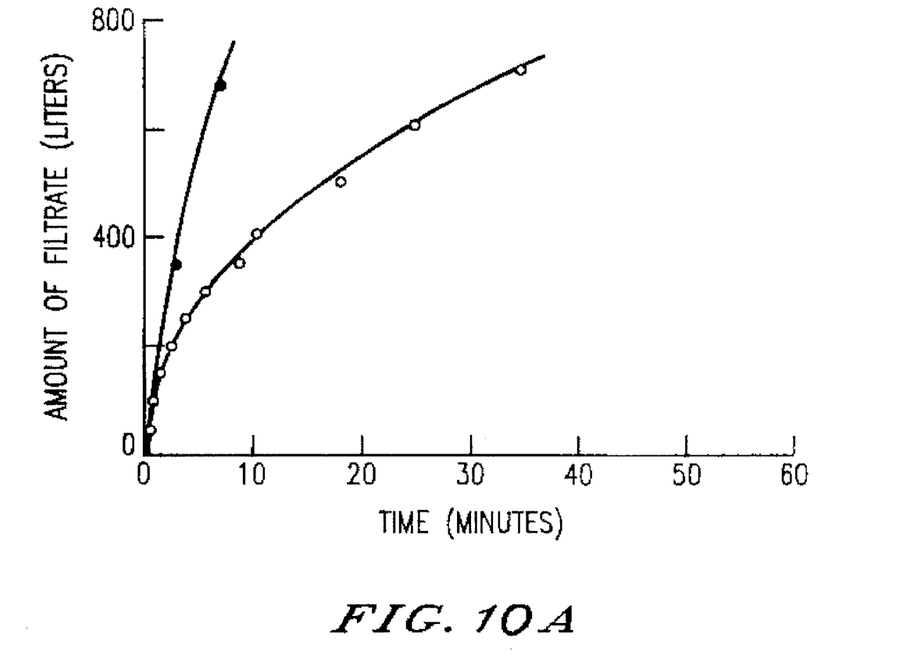
FIG. 10A and FIG. 10B show a comparison between the filtration rate and dehydration rate characteristics of aspartame crystals obtained in (i) the unagitated process used in the present invention and (ii) an agitated crystallization process.
Figure 10B:
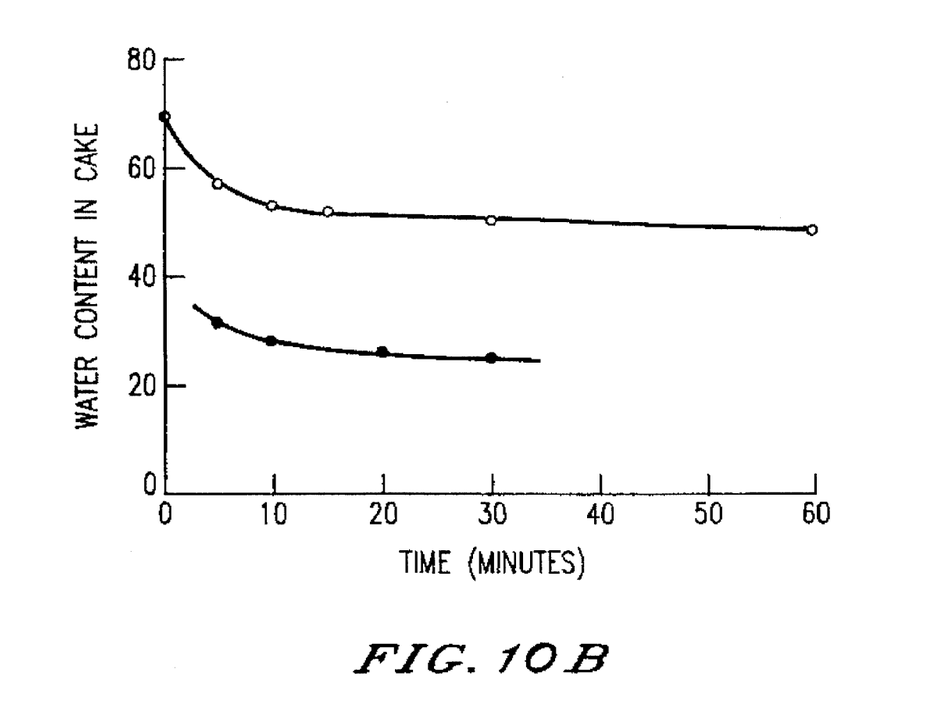

A comparison of the results obtained with the process of the present invention and with the conventional process with respect to centrifuge-filtration rate and centrifuge dewatering rate are shown in FIG. 10A and FIG. 10B, respectively. The solid circles show the values obtained with the aspartame slurry obtained in accordance with the unagitated process. The empty circles show the values obtained with the aspartame slurry obtained by the agitated process.

In a leaf test by suction filtration to determine specific resistance value, the aspartame slurry obtained by the unagitated process showed a specific resistance of $1 \times 10^8$ to $2 \times 10^8$ m Kg$^{-1}$ immediately after being discharged and $3 \times 10^8$ to $5 \times 10^8$ m Kg$^{-1}$ after desupersaturation. The slurry obtained by the agitated process showed a specific resistance of $5 \times 10^{10}$ to $1 \times 10^{11}$ m Kg$^{-1}$.

Example 4

Figure 11:
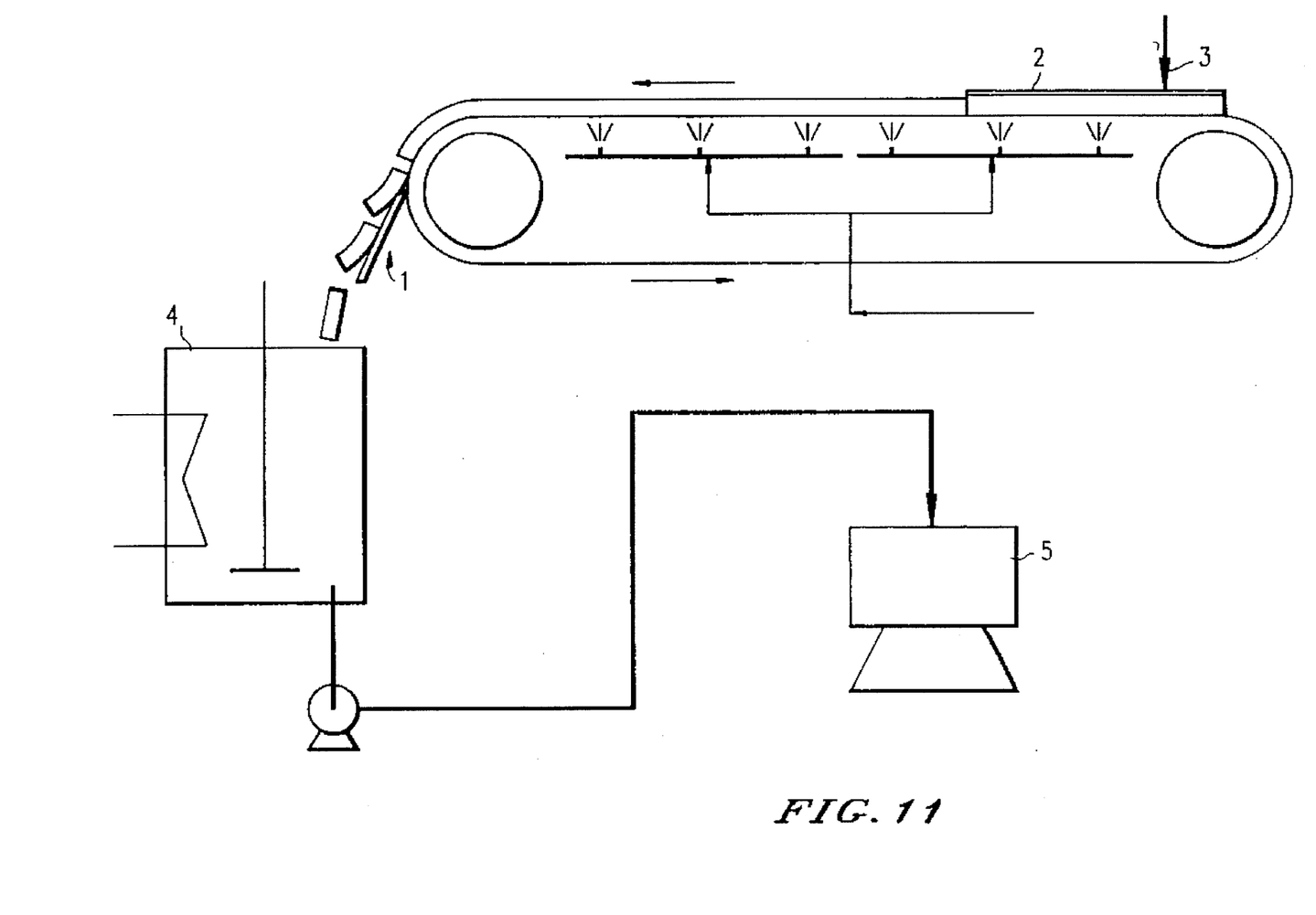
FIG. 11 shows the crystallizer used in Example 2.

A feed solution having the same composition as in Example 3 was cooled using a steel belt cooler (1.2 m×5 m; made by stainless steel) as shown in FIG. 11 to crystallize aspartame. The feed solution was continuously introduced onto the belt through feed inlet 3. Where the feed amount is large, it is preferable to provide guides 2 on the sides of the belt to prevent overflow. In such cases, the guides are not necessarily provided over the full length of the belt, because the solution does not flow out after the sherbet-like solid forms.

Cooling was conducted indirectly by jetting 12° C. cooling water to the back of the belt. The solution-feeding rate and the belt speed were adjusted so that the thickness of sherbet, or maximum distance from the cooling surface, was about 10 mm.

The thus obtained sherbet containing aspartame crystals and water was scraped out by scraper 1 and destroyed in receiving tank 4 by stirring (60 r.p.m.) into a slurry. The average temperature of the product immediately after scraping was about 18° C. Additionally, cooling for desupersaturation was not particularly conducted in the receiving tank.

When about 100 liters of the slurry in the receiving tank was subjected to solid-liquid separation in centrifugal separator 5, the water content of cake was reduced to about 30% after 30 minutes. Yield: 4.3 Kg. The separated mother liquor contained about 1.5 wt % aspartame. Recovery ratio: 68%.

This steel-belt cooler system has the advantages that, as compared to the system of Example 3, the cooling surface can be smaller due to larger processing speed and that, in view of process flow, a feed solution is not necessarily kept at high temperature because of continuous system, thus the decomposition of aspartame is remarkably reduced.

Obviously, numerous modifications and variations of the present invention are possible in light of the above teachings. It is therefore to be understood that within the scope of the appended claims, the invention may be practiced otherwise than as specifically described herein.

What is claimed is:

1. A process for obtaining dry crystals of α-L-aspartyl-L-phenylalanine methyl ester, comprising:

i) exposing wet crystals of α-L-aspartyl-L-phenylalanine methyl ester, having a water content not greater than 50 wt. % based on the weight of the wet crystals and obtained by the crystallization of α-L-aspartyl-L-phenylalanine methyl ester from an unagitated solution of α-L-aspartyl-L-phenylalanine methyl ester, to a flow of air having a temperature of from 80°–200° C.; and ii) obtaining α-L-aspartyl-L-phenylalanine methyl ester crystals having a water content of about 2.6 wt. % to about 6 wt. % based on the weight of the wet crystals.

2. The process of claim 1, comprising exposing wet crystals to said flow of air in a drying means having an air flow inlet means and an air flow outlet means, wherein the air temperatures at said inlet means is from 80° to 200° C. and the air temperature at said outlet means is 50° to 180° C.

3. The process of claim 2, wherein said air temperature at said outlet means is 50° to 104° C.

4. A process for obtaining dry crystals of α-L-aspartyl-L-phenylalanine methyl ester, comprising:

i) obtaining wet crystals of α-L-aspartyl-L-phenylalanine methyl ester, having a water content not greater than 50 wt. % based on the weight of the wet crystals, by the crystallization of α-L-aspartyl-phenylalanine methyl ester from an unagitated solution of α-L-aspartyl-L-phenylalanine methyl ester;

ii) exposing said wet crystals to a flow of air having a temperature of from 80°–200° C.; and iii) obtaining α-L-aspartyl-L-phenylalanine methyl ester crystals having a water content of about 2.6 wt. % to about 6 wt. % based on the weight of the wet crystals.

5. The process of claim 4, comprising exposing wet crystals to said flow of air in a drying means having an air flow inlet means and an air flow outlet means, wherein the air temperatures at said inlet means is from 80° to 200° C. and the air temperature at said outlet means is 50° to 180° C.

6. The process of claim 5, wherein said air temperature at said outlet means is 50° to 104° C.

7. The process of claim 1, comprising using wet crystals having a water content of not greater than 20 wt. %.

8. The process of claim 1, comprising using wet crystals having a water content of from approximately 10 wt. % to 20 wt. %.

9. The process of claim 1, wherein said process is continuous and comprises exposing said wet crystals to said flow of air at a residence time of not more than about 1 minute.

10. The process of claim 1, comprising exposing said wet crystals to said flow of air at a residence time of not more than about 1 minute.

11. The process of claim 4, comprising using wet crystals having a water content of not greater than 20 wt. %.

12. The process of claim 4, comprising using wet crystals having a water content of from approximately 10 wt. % to 20 wt. %.

13. The process of claim 4, comprising exposing said wet crystals to said flow of air for a length of time of not more than about 1 minute.

14. The process of claim 4, comprising using wet crystals having a water content of not greater than 30 wt. %.

15. The process of claim 1, comprising using wet crystals having a water content of not greater than 30 wt. %.

16. The process of claim 14, wherein said process is continuous and comprises exposing said wet crystals to a flow of air at a residence time of not more than about 1 minute.

* * * * *